United States Patent
Douget et al.

(10) Patent No.: US 8,845,689 B2
(45) Date of Patent: Sep. 30, 2014

(54) SYSTEM FOR STABILIZING AT LEAST A PORTION OF THE SPINE

(75) Inventors: Stephane Douget, Bouscat (FR); Vincent Pointillart, Bordeaux (FR)

(73) Assignee: Zimmer Spine S.A.S., Bordeaux (FR)

( * ) Notice: Subject to any disclaimer, the term of this patent is extended or adjusted under 35 U.S.C. 154(b) by 878 days.

(21) Appl. No.: 12/429,840

(22) Filed: Apr. 24, 2009

(65) Prior Publication Data
US 2009/0270920 A1 Oct. 29, 2009

(30) Foreign Application Priority Data
Apr. 24, 2008 (EP) .................................... 08305124

(51) Int. Cl.
*A61B 17/70* (2006.01)
*A61B 17/84* (2006.01)

(52) U.S. Cl.
CPC ........... *A61B 17/7055* (2013.01); *A61B 17/842* (2013.01); *A61B 17/7011* (2013.01); *A61B 17/7062* (2013.01); *A61B 17/7067* (2013.01)
USPC .......................................... 606/249; 606/248

(58) Field of Classification Search
USPC ................................................. 606/246–279
See application file for complete search history.

(56) References Cited

U.S. PATENT DOCUMENTS

| | | |
|---|---|---|
| 902,040 A | 10/1908 | Wychoff |
| 1,346,940 A | 7/1920 | Collins |
| 2,049,361 A | 7/1936 | Ericsson |
| 5,030,220 A | 7/1991 | Howland |
| 5,356,412 A | 10/1994 | Golds et al. |
| 5,413,576 A | 5/1995 | Rivard |
| 5,609,634 A * | 3/1997 | Voydeville ................. 623/13.11 |
| 5,667,508 A | 9/1997 | Errico et al. |
| 5,702,399 A | 12/1997 | Kilpeta et al. |
| 5,935,133 A | 8/1999 | Wagner et al. |
| 5,938,663 A | 8/1999 | Petreto |

(Continued)

FOREIGN PATENT DOCUMENTS

| | | |
|---|---|---|
| DE | 19716504 | 12/1998 |
| EP | 0780096 | 6/1997 |

(Continued)

OTHER PUBLICATIONS

International Search Report and Written Opinion for PCT Application No. PCT/EP2008/062791, completed Nov. 18, 2008, mailed Dec. 4, 2008, 10 pages.

(Continued)

*Primary Examiner* — Jerry Cumberledge
*Assistant Examiner* — Nicholas Plionis
(74) *Attorney, Agent, or Firm* — Seager, Tufle & Wickhem, LLC (57) ABSTRACT

Disclosed are embodiments of a dynamic stabilizer system for dynamically stabilizing the sacrum and at least lumbar vertebra L5. The dynamic stabilizer system may comprise two anchoring members that can be implanted at distinct locations in the sacrum, a mechanical fastener element having two ends and a flexible portion that can be securely fastened on the spinous process of a lumbar vertebra, and two distinct rods, each securing onto the anchoring members and the mechanical fastener element. In some embodiments, the dynamic stabilizer system may further comprise one or more spacers, each interposed between two spinous processes. The mechanical fastener element further comprises features for securing the one or more spacers.

15 Claims, 7 Drawing Sheets

(56) References Cited

U.S. PATENT DOCUMENTS

| | | | |
|---|---|---|---|
| 5,964,769 | A | 10/1999 | Wagner et al. |
| 6,053,921 | A | 4/2000 | Wagner et al. |
| 6,086,590 | A | 7/2000 | Margulies et al. |
| 6,099,527 | A | 8/2000 | Hochschuler et al. |
| 6,179,838 | B1 | 1/2001 | Fiz |
| 6,352,557 | B1 | 3/2002 | Ferree |
| 6,391,030 | B1 | 5/2002 | Wagner et al. |
| 6,419,702 | B1 | 7/2002 | Ferree |
| 6,478,798 | B1 | 11/2002 | Howland |
| 6,514,255 | B1 | 2/2003 | Ferree |
| 6,547,770 | B2 | 4/2003 | Carlsson et al. |
| 6,569,164 | B1 | 5/2003 | Assaker et al. |
| 6,616,669 | B2 | 9/2003 | Ogilvie et al. |
| 6,682,533 | B1 | 1/2004 | Dinsdale et al. |
| 6,723,335 | B1 | 4/2004 | Ranieri |
| 6,946,000 | B2 | 9/2005 | Senegas et al. |
| 2002/0116013 | A1 | 8/2002 | Gleason et al. |
| 2004/0097942 | A1 | 5/2004 | Allen et al. |
| 2004/0138666 | A1 | 7/2004 | Molz, IV et al. |
| 2005/0085815 | A1 | 4/2005 | Harms |
| 2005/0228375 | A1* | 10/2005 | Mazda et al. ............ 606/61 |
| 2005/0273983 | A1 | 12/2005 | Mattchen |
| 2006/0235387 | A1 | 10/2006 | Peterman |
| 2006/0235391 | A1 | 10/2006 | Sutterlin, III |
| 2007/0191834 | A1* | 8/2007 | Bruneau et al. ............ 606/61 |
| 2007/0299445 | A1 | 12/2007 | Shadduck et al. |
| 2008/0033557 | A1 | 2/2008 | Pasquet et al. |
| 2008/0114357 | A1* | 5/2008 | Allard et al. ............ 606/61 |
| 2008/0125780 | A1 | 5/2008 | Ferree |
| 2008/0208256 | A1 | 8/2008 | Thramann |

FOREIGN PATENT DOCUMENTS

| | | |
|---|---|---|
| EP | 1815812 | 8/2007 |
| FR | 522040 | 7/1921 |
| FR | 26156 | 9/1932 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| FR | 2897771 A1 | 8/2007 |
| GB | 2269753 | 2/2004 |
| JP | 2001299770 | 10/2001 |
| WO | WO 9416635 A1 | 8/1994 |
| WO | WO 02/07621 A | 1/2002 |
| WO | WO 02/07622 A | 1/2002 |
| WO | WO 0209604 A1 | 2/2002 |
| WO | WO 0217803 A2 | 3/2002 |
| WO | WO 02051326 A1 | 7/2002 |
| WO | WO 02071960 A1 | 9/2002 |
| WO | WO03/007829 A1 | 1/2003 |
| WO | WO 03007829 A1 | 1/2003 |
| WO | WO 03103519 A1 | 12/2003 |
| WO | WO 2004010881 A1 | 2/2004 |
| WO | WO 2005/020860 A3 | 3/2005 |
| WO | WO 2005020860 A3 | 3/2005 |
| WO | WO 2005120277 A1 | 12/2005 |
| WO | WO2006034423 A2 | 3/2006 |
| WO | WO 2006/106268 A3 | 10/2006 |
| WO | WO 2006106268 A3 | 10/2006 |
| WO | WO 2006106246 | 12/2006 |
| WO | WO 2007/023240 A3 | 3/2007 |
| WO | WO 2007023240 A3 | 3/2007 |
| WO | WO 2007034112 A1 | 3/2007 |
| WO | WO 200736657 | 4/2007 |
| WO | WO 2007099258 A2 | 9/2007 |
| WO | WO2009130276 A1 | 10/2009 |
| WO | WO2009141393 A1 | 11/2009 |

OTHER PUBLICATIONS

French Preliminary Search Report for French Application No. 0757814, issued May 22, 2008, 2 pgs.

International Preliminary Report on Patentability issued in International Patent Application No. PCT/EP2008/062791, Mar. 30, 2010, 7 pages.

European Search Report for EP 08 30 5124, 3 pages, dated Oct. 10, 2008.

French Preliminary Search Report for FR 0405611, 2 pages, dated Jan. 12, 2005.

International Search Report for PCT/FR2005/001280, 3 pages, dated Nov. 7, 2005.

Written Opinion for PCT/FR2005/001280, 6 pages, dated Nov. 25, 2006.

European Search Report for EP 08305124.3, dated Oct. 20, 2008, 3 pages.

English Translation of International Preliminary Report for PCT/FR2006/050898 on Patentability Chapter I, dated Apr. 29, 2008, 6 pages.

English Translation of International Preliminary Report on Patentability Chapter I for PCT/FR2006/050909, dated Apr. 8, 2008, 5 pages.

English Translation of the Written Opinion of the International Search Authority for PCT/FR2006/050909, dated Apr. 2, 2008, 4 pages.

English Translation of the Written Opinion of the International Search Authority for PCT/FR2006/050898, dated Apr. 28, 2008, 5 pages.

European Search Report for EP 08305183, dated Mar. 19, 2009, 10 pages.

European Search Report for EP 08305326, dated Nov. 12, 2008, 3 pages.

European Search Report for EP 2052689, dated Apr. 15, 2008, 6 pages.

European Search Report issued in EP 08305326 on Nov. 18, 2006, 5 pages.

French Preliminary Search Report and Written Opinion for FR200650609, dated Jun. 30, 2006, 5 pages.

International Search Report for WO2009053423, dated May 19, 2009, 4 pages.

International Search Report mailed Nov. 24, 2008 for PCT/EP2008/063682, 3 pages.

International Search Report for PCT/FR2006/050909 published as WO/2007/034112, dated Jan. 24, 2007, 3 pages.

Office Action for U.S. Appl. No. 10/521,914, dated Dec. 29, 2006, 21 pages.

Office Action for U.S. Appl. No. 10/521,914, dated Mar. 19, 2008, 7 pages.

Office Action for U.S. Appl. 10/521,914, dated Jun. 16, 2006, 13 pages.

Office Action for U.S. Appl. No. 10/521,914, dated Jul. 30, 2007, 13 pages.

International Search Report and Written Opinion for PCT/US2009/038977, mailed Jul. 22, 2009, 13 pages.

Korean Examination report for Korean Patent Application No. 1020057001238, mailed Feb. 23, 2010, 3 pages.

French Preliminary Search Report for FR0209317, dated Apr. 9, 2003, 1 page.

French Preliminary Search Report for FR0509629 mailed Jun. 9, 2006, 2 pages.

International Search Report for FR200302307, dated Jan. 2, 2004, 2 pages.

Australian Search Report for 2003267529, dated Nov. 15, 2007, 2 pages.

French Preliminary Search Report FR0509570, dated Jun. 29, 2006, 2 pages.

International Search Report for PCT/FR2006/050898, dated Feb. 2, 2007, 2 pages.

Written Opinion for PCT/US2009/038977, mailed Feb. 24, 2010, 7 pages.

European Search Report for European Patent Application No. 07 301 454.0, mailed Sep. 25, 2008, 8 pages.

* cited by examiner

SYSTEM FOR STABILIZING AT LEAST A PORTION OF THE SPINE

CROSS-REFERENCE TO RELATED APPLICATION

This application claims a benefit of priority under 35 U.S.C. 119(a) of the filing date of European Patent Application No. 08305124, entitled "System for Stabilizing at Least a Portion of the Spine" by inventors Stephane Douget and Vincent Pointillart, filed on Apr. 24, 2008, the content of which application is hereby incorporated as if fully set forth herein.

TECHNICAL FIELD OF THE DISCLOSURE

The present disclosure includes a system and method for stabilizing at least a portion of the spine, including in at least one embodiment a system for dynamically stabilizing the sacrum and at least lumbar vertebra L5.

SUMMARY OF THE DISCLOSURE

PCT patent applications Nos. WO 2005/020860, WO 2006/106268, and WO 2007/023240, which are incorporated herein by reference, describe systems for stabilizing the sacrum to the fifth lumbar vertebra.

Those devices are very effective, but they prevent the vertebra(e) from moving relative to the sacrum in a manner that is practically total, thus leaving no degree of freedom between the sacrum and the last lumbar vertebra. In many circumstances, that situation is unfavorable.

To solve this problem, at least one object of the present disclosure is to provide a system for stabilizing the sacrum and at least the fifth lumbar vertebra that makes dynamic stabilization possible. For this particular embodiment of the disclosure, the term "dynamic stabilization" is used to mean that the sacrum and at least the last lumbar vertebra are indeed stabilized relative to each other, but that a limited amount of relative movement is nevertheless allowed between the vertebra and the sacrum so as to enable the patient to be more comfortable.

According to the disclosure, to achieve this particular object, a dynamic stabilizer system for dynamically stabilizing the sacrum and at least lumbar vertebra L5, is characterized in that it comprises:
  two anchoring members in the sacrum, said members being implanted at distinct locations;
  two distinct rigid rods, each presenting a first end and a second end, each second end being secured to an anchoring member in such a manner that the point at which each rod is secured close to its second end can be adjusted; and
  a mechanical fastener element fastened on the process of a lumbar vertebra, said mechanical fastener element presenting a first end and a second end, the first end of each rigid rod being secured to one of the ends of said mechanical fastener element, said mechanical fastener element including a flexible portion.

It will be understood that by means of the disclosure, effective stabilization is obtained for the vertebra(e) relative to the sacrum, in particular because of the presence of the two rigid rods, each of which is anchored at one end to the sacrum by the mechanical fastener element, and each of which is connected at its other end to the spinous process of at least the fifth lumbar vertebra, with adjustment being possible. The reader should appreciate that the mechanical fastener element may be a screw, nail, or any other type of fastener capable for fixation to bone. Nevertheless, since the mechanical fastener element includes a flexible portion connecting the process to one of the ends of the rigid rods, dynamic stabilization is indeed obtained that allows limited amounts of relative movement between the sacrum and the lumbar vertebra(e).

In a first embodiment, said mechanical fastener element includes at least one flexible tie completely surrounding the spinous process of the vertebra L5, said first and second ends of said mechanical fastener element being constituted by portions of said tie(s).

It will be understood that under such circumstances, the spinous process of the fifth lumbar vertebra is surrounded by one or more flexible ties and that the second ends of said rigid rods are rigidly anchored in the sacrum by the anchoring members. The dynamic stabilization is obtained by the presence of the tie(s) surrounding the process.

In a second embodiment, said mechanical fastener element comprises at least a first spacer interposed between the process of lumbar vertebra L5 and the process S1 of the sacrum, said spacer presenting said first and second ends; and a flexible tie co-operating with the process of a lumbar vertebra, said flexible tie presenting two ends secured to said spacer.

It will be understood that the stabilization between the sacrum and the last lumbar vertebra is obtained by co-operation between the spacer with the two rigid rods, each having one end anchored in the sacrum, and with the flexible tie that co-operates with the process of at least the fifth lumbar vertebra. This procures effective stabilization, while allowing limited amounts of relative movement between the vertebra and the sacrum by using the flexible tie in co-operation with the process of the vertebra or the processes of the vertebrae.

In a variant embodiment, said mechanical fastener element further comprises a second spacer interposed between the processes of lumbar vertebrae L5 and L4, said flexible tie co-operating with said second spacer and partially surrounding the process of lumbar vertebra L4.

It will be understood that because of the presence of the second spacer, the tie enables both the fifth and the fourth lumbar vertebrae to be stabilized with the sacrum, while also allowing relative movement between the sacrum, the fifth lumbar vertebra, and the fourth lumbar vertebra. Naturally, it is possible to provide more than one second spacer should it be appropriate to stabilize more than two vertebrae with the sacrum.

Other characteristics and advantages of the disclosure appear better on reading the following description of various embodiments of the disclosure given as non-limiting examples.

BRIEF DESCRIPTION OF THE DRAWINGS

The description refers to the accompanying figures, in which.

DETAILED DESCRIPTION

Figure 1:
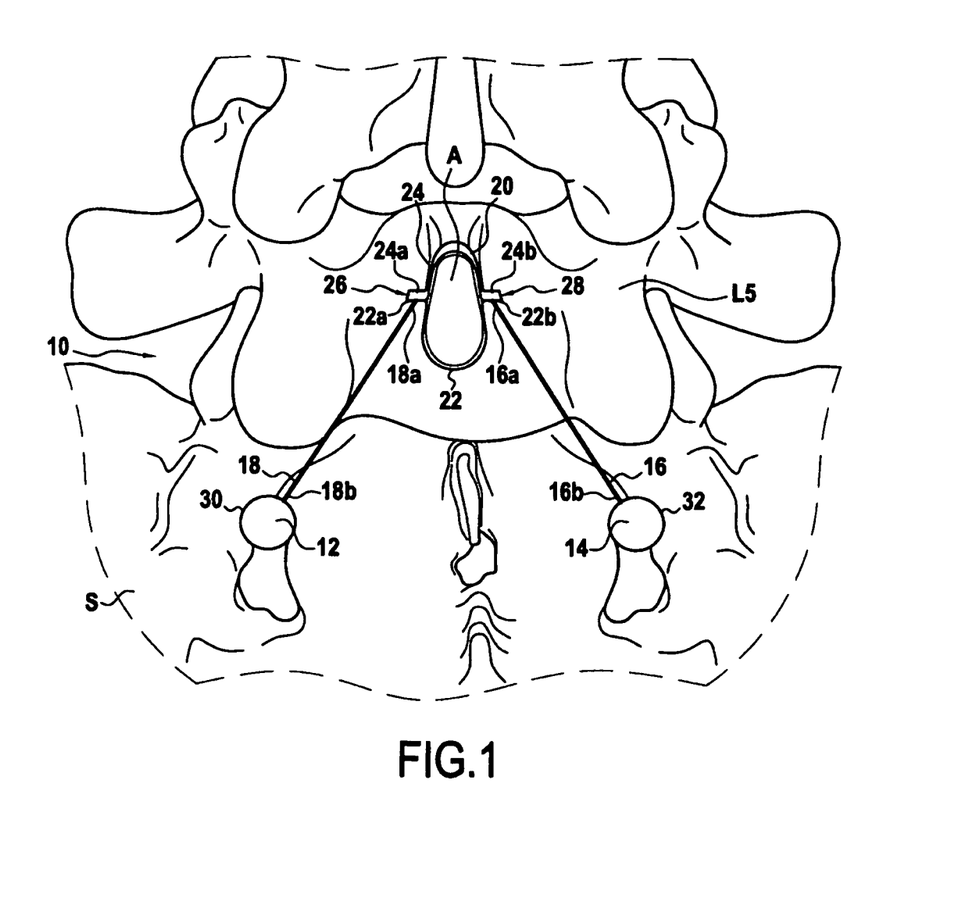
FIG. 1 is a perspective view of a first embodiment of the dynamic stabilizer system.

With reference initially to FIG. 1, there follows a description of a first embodiment of the dynamic stabilizer system.

In this figure, there can be seen the upper portion of the sacrum S together with the lower lumbar vertebra L5 and its spinous process A.

The dynamic stabilizer system, given overall reference 10, is constituted by two anchoring members 12 and 14 preferably constituted by screws screwed into the sacrum, by two rigid rods 16 and 18, and by a mechanical fastener element fastened to the process A, and given reference 20. As explained above, the mechanical element fastened to the process includes a flexible portion that is constituted, in this embodiment, by two flexible tie portions 22 and 24. The ends 22a, 22b and 24a, 24b of these ties are secured to one another in such a manner that the assembly constituted by the tie portions 22 and 24 completely surrounds the spinous process A. The ends 22a, 24a and 22b, 24b of the tie portions constitute fastener ends of the mechanical fastener element 20, which fastener ends are fastened to the first ends 16a and 18a of the rigid rods 16 and 18. A preferred embodiment of the securing means between the ends of the rods 16 and 18 and the ends 26 and 28 of the mechanical fastener element 20 are described in greater detail below. The anchoring members 12 and 14, which are preferably constituted by screws 30 and 32 screwed into suitable portions of the sacrum, are described in greater detail below. They serve to fasten the second ends 16b and 18b of the rigid rods 16 and 18. The screws 30 and 32 cooperate with the ends 16b and 18b of the rigid rods in such a manner that, prior to the ends being secured on the screws, it is possible to adjust which portions of the rigid rods that are indeed held securely. In other words, it is possible to adjust the distance between the ends 16a and 18a of the rods and the zones in which the anchoring elements are clamped onto the rods.

This makes it possible to adjust the stabilization effect between the lumbar vertebra L5 and the sacrum S.

It will be understood that since the connection between the first ends 16a and 18a of the rigid rods 16 and 18 and the spinous process A of the lumbar vertebra L5 is provided via tie portions 22 and 24 that are flexible, the vertebra L5 is indeed stabilized dynamically relative to the sacrum, such that limited relative movement remains possible between the vertebra L5 and the sacrum S. The tie portions are made using a material that presents sufficient flexibility, and possibly also sufficient elasticity, to allow limited relative movement. For example, the material may be a polyester, a polyethylene, polyetheretherketone (PEEK) or any other material that provides the desired elasticity.

Figure 1A:
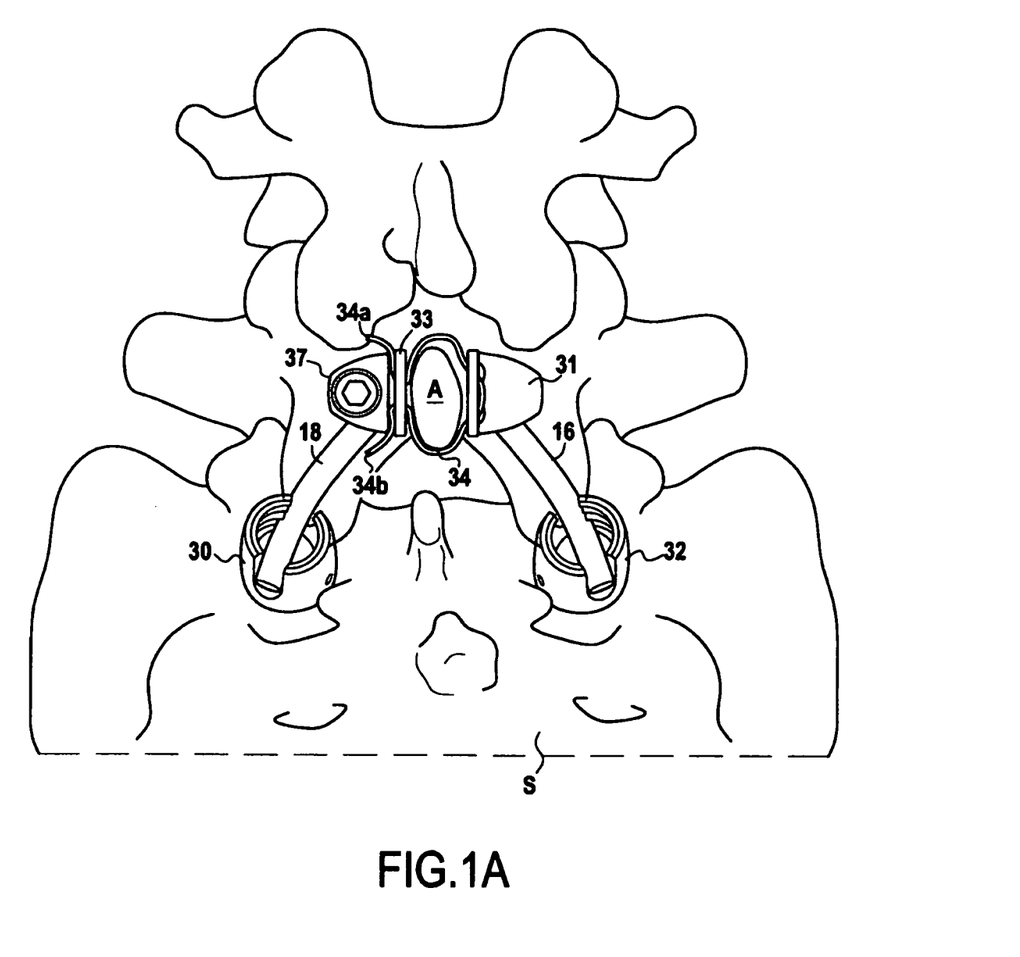
FIG. 1A shows an embodiment of the connection between the rigid rods and the mechanical fastener element for the embodiment of FIG. 1.
Figure 1B:
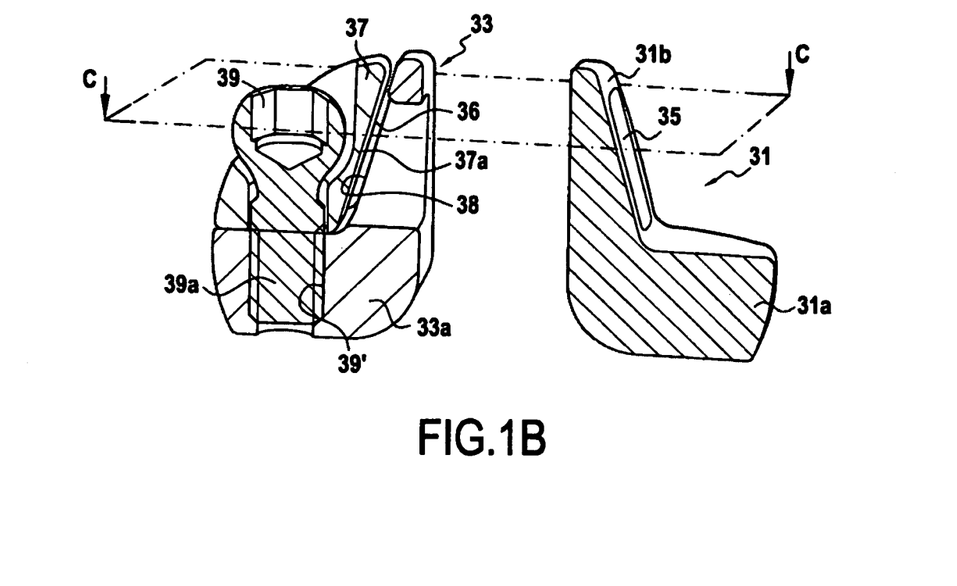
FIG. 1B is a vertical section view showing two fastener parts of the FIG. 1A embodiment.
Figure 1C:
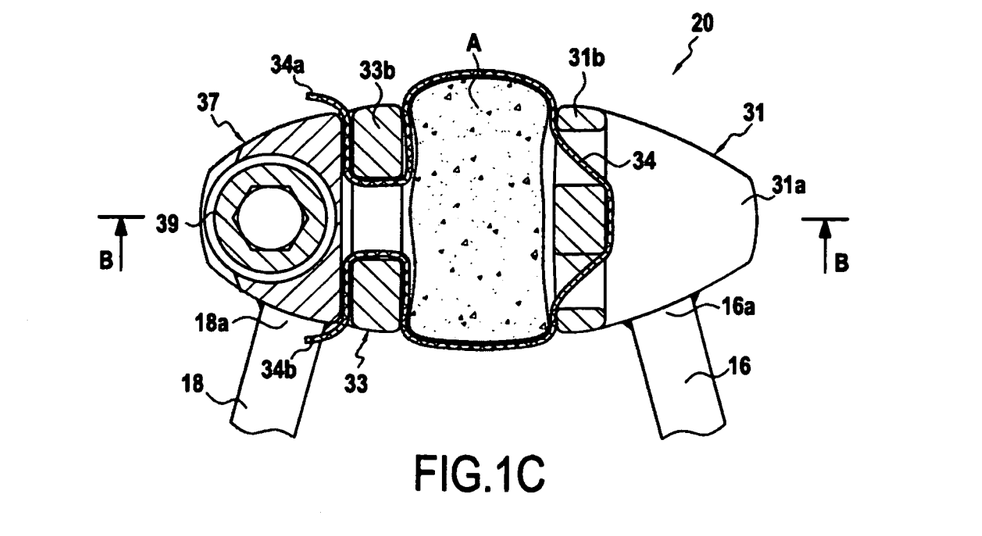
FIG. 1C is a plan view of the mechanical connection system of FIG. 1A.

FIGS. 1A, 1B, and 1C show a particular embodiment of the mechanical element 20 for fastening to the process.

The mechanical element 20 is essentially constituted by two securing parts 31 and 33 and by a flexible tie or braid 34 that performs the same function as the tie portions 22 and 24 in FIG. 1. The securing parts 31 and 33 are designed to be fastened on either side of the spinous process A with the help of the braid 34.

Each securing part comprises a main portion 31a, 33a and a lug 31b, 33b extending substantially perpendicularly to the main portion. The lugs 31b, 33b are held by the braid 34 against the sides of the process A. The lugs 31b and 33b have slots 35, 36 for passing the braid 34. The ends 16a, 18a of the rigid rods 16, 18 are welded to the main portions 31a, 33a of the parts 31, 33.

In order to secure or block the free ends 34a and 34b of the braid 34, the part 33 is provided with a movable clamping member 37. The clamping member 37 presents a clamping face 37a facing the sloping face 38 of the lug 33b of the part 33. A screw 39 passes freely through the clamping member 37 and its threaded portion 39a co-operates with a tapped hole 39' formed in the main portion 33a of the fastener part 33.

By tightening the screw 39, the clamping surface 37a is caused to move towards the clamping surface 38 of the lug 33b. This thus secures the ends 34a, 34b of the braid to the parts 31 and 33. Nevertheless, since the braid 34 is flexible, limited movement remains possible between the process A and the parts 31 and 33, i.e. limited relative movement is possible between the vertebra and the sacrum.

Figure 2:
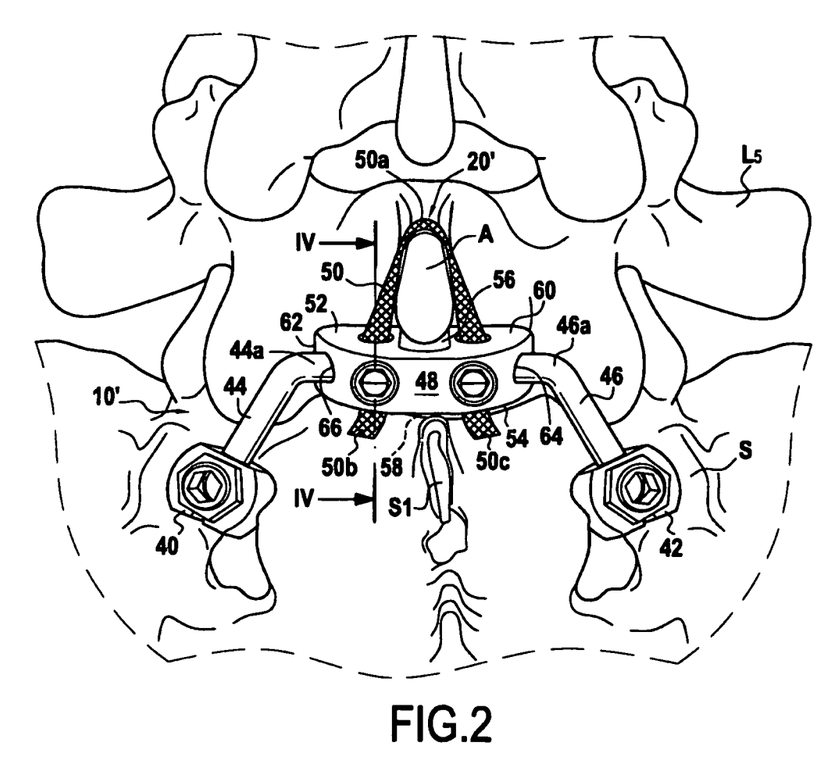
FIG. 2 is a perspective view of a second embodiment of the dynamic stabilizer system.
Figure 3:
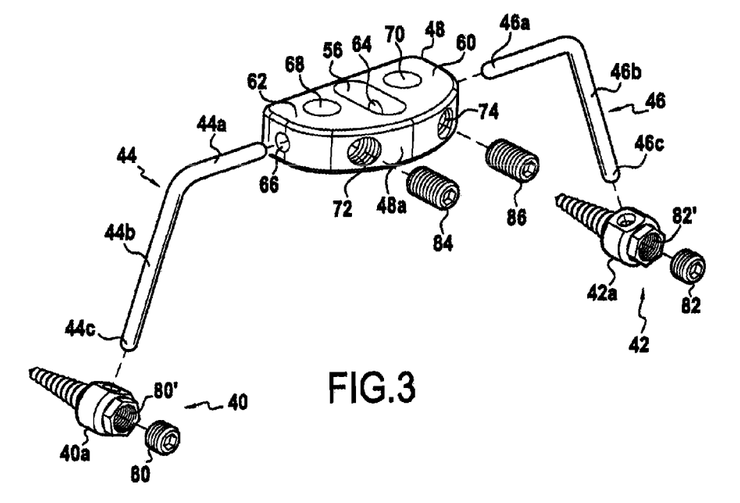
FIG. 3 is an exploded view showing the connection between the spacer shown in FIG. 2 and the rigid rods.
Figure 4:
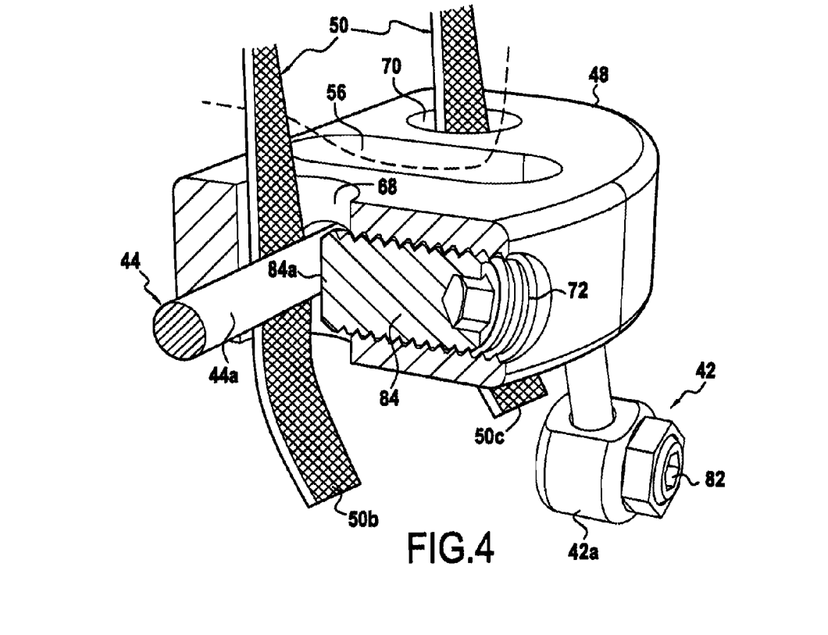
FIG. 4 is a perspective view, partially in section on plane IV-IV of FIG. 2, showing how the ends of the rods and the ends of the flexible tie are secured.

FIGS. 2 to 4 show a second embodiment of the disclosure that is described below.

In this second embodiment, the dynamic stabilizer system is given reference 10' and it is constituted by two screws 40 and 42 that constitute the anchoring members in the sacrum S, by two rigid rods 44 and 46, and by a mechanical fastener element referenced 20' for fastening to the spinous process A of the vertebra L5. In this embodiment, the mechanical fastener element 20' is essentially constituted by an intervertebral spacer 48 and by a flexible tie 50.

The spacer 48 is interposed between the spinous process A of the vertebra L5 and the spinous process S1 of the sacrum S. More precisely, the spacer 48 has two end portions 52 and 54, each provided with a recess 56, 58 for receiving the spinous processes A and S1. As explained in greater detail below, the spacer 48 serves both for fastening to one of the ends of each of the rigid rods 44 and 46, and for securing the ends of the flexible braid 50.

Preferably, the spacer 48 is elongate in shape in a direction perpendicular to the axis of the spine and includes a first end 60 and a second end 62. Each of these ends 60 and 62 is pierced by a respective orifice 64, 66 into which the ends 46a and 44a of the rods 44 and 46 can penetrate.

Close to its ends 60 and 62, the spacer 48 also has two orifices 68 and 70 that pass right through the spacer in its thickness direction, i.e. between its faces 52 and 54. These orifices 68 and 70 communicate with the end orifices 64 and 66. Finally, tapped holes 72 and 74 are provided in the side face 48a of the spacer 48. These tapped holes 72 and 74 also open out into the orifices 68 and 70.

When the dynamic stabilizer system is put into place, the flexible tie or braid 50 has its middle portion 50a that bears against the top face of the spinous process A of the vertebra L5 and has portions close to the ends 50b and 50c that are engaged in the orifices 68 and 70 so as to project beyond the spacer 48.

Finally, as can be seen better in FIG. 3, it should be observed that each rod has a first end 44a, 46a that is angled relative to the main portion 44b, 46b of each of the rods, with the second end of each rod having a respective reference 44c and 46c.

The screws 40 and 42 can be screws of the same type as the screws 30 and 32 as used in the first embodiment of the disclosure, and as described in greater detail below, and they enable adjustment to be performed.

There follows a description of how the dynamic stabilizer system 10' is put into place by the surgeon.

After performing anatomic operations giving access to the lumbar vertebra L5 and to the upper portion of the sacrum S, the surgeon puts the spacer 48 into place between the process A of the lumbar vertebra L5 and the process S1 of the sacrum in such a manner that these processes are received in the recesses 56 and 58 of the spacer. Thereafter, the surgeon screws the screws 40 and 42 into the sacrum. The ends 46c and 46c of the rigid rods 44 and 46 are put into place in the heads of the screws. The flexible braid 50 is then put into place in such a manner that its middle portion 50a bears against the top face of the spinous process A of the lumbar vertebra L5, and the two ends of the braid are caused to penetrate into the through orifices 68 and 70 so that the free ends 50b and 50c of the braid project beyond the bottom face of the spacer 48. The surgeon inserts the ends 44a and 46a of the rigid rods 44 and 46 into the end orifices 64 and 66 of the spacer 48. The surgeon can adjust stabilization by inserting the ends 44c and 46c to a greater or lesser extent into the heads 40a and 42a of the screws 40 and 42. Once adjustment has been achieved in satisfactory manner, i.e. once the desired degree of stabilization has been reached, the surgeon secures the screws 40 and 42 to the ends 44c and 46c of the rigid rods with the help of headless set screws 80 and 82 co-operating with tapped holes 80' and 82' formed in the heads of the screws 40 and 42.

Thereafter, by inserting headless set screws 84 and 86 in the tapped holes 72 and 74, the surgeon proceeds to secure the ends of the flexible braid 50 of the spacer 48 and the second ends 44a and 46a of the rigid rods 44 and 46. As shown better in FIG. 4, an intermediate portion of the braid 50 engaged in the orifice 68 is placed between the end 44a of the rigid rod 44 and the wall of the orifice 68. By acting on the set screw 84 engaged in the tapped hole 72, the end 84a of the screw 84 exerts pressure on the end 44a of the rod 44 and on the intermediate portion of the braid 50. Before ensuring that these various parts are finally blocked in position, the surgeon applies suitable traction on the ends 50b and 50c of the braid 50 in order to obtain the desired degree of stabilization and also the desired possibilities for relative movement between the sacrum and the vertebra L5, i.e. the desired dynamic stabilization. This traction may advantageously be exerted with the help of the traction instrument described in PCT patent application WO 2007/034112, which is incorporated herein by reference. When the set screws 84 and 86 are engaged to the maximum, the spacer 48, the ends of the braid 50, and the ends of the rigid rods 44 and 46 are secured effectively to one another.

Figure 5:
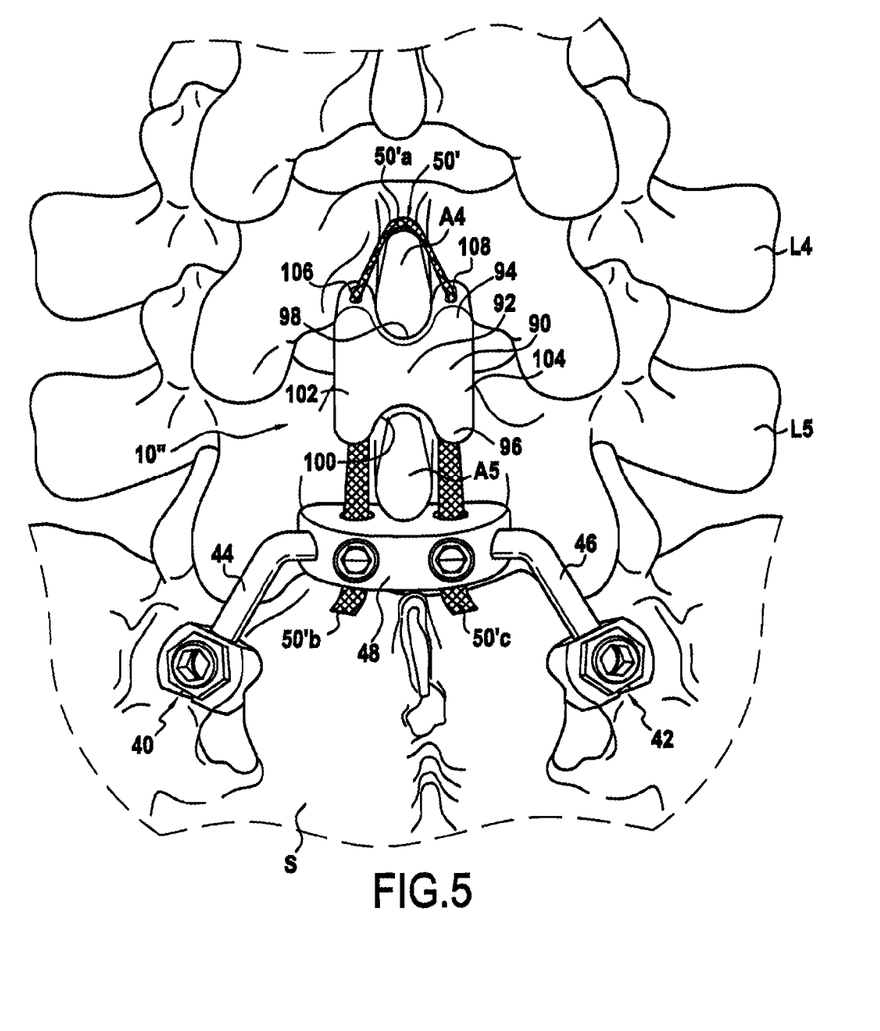
FIG. 5 is a perspective view of a variant of the second embodiment enabling two vertebrae to be stabilized dynamically relative to the sacrum.

With reference to FIG. 5, there follows a description of a variant of the second embodiment of the dynamic stabilizer system that makes it possible to obtain stabilization between the sacrum S and both lumbar vertebrae L5 and L4. The dynamic stabilizer system, now referenced 10", has anchor screws 40 and 42 in the sacrum, a spacer 48, and rigid rods 44 and 46. All of these elements are analogous or identical to those described above with reference to the embodiment of FIGS. 2 to 4. The essential difference lies in the length of the flexible braid 50' and in the addition of a simple intervertebral spacer 90 which is interposed between the spinous process A4 of the lumbar vertebra L4 and the spinous process A5 of the lumbar vertebra L5. In conventional manner, the intermediate spacer 90 comprises an intermediate portion 92 that may present a certain amount of flexibility, and two end portions 94 and 96, each defining a recess 98 or 100 for receiving a respective one of the spinous processes A4 and A5. In its side portions 102 and 104, the simple intervertebral spacer 90 has two passages 106 and 108 extending along the entire length of the spacer in the axial direction of the spine.

The middle portion 50'a of the flexible tie or braid 50' passes over the top face of the spinous process A4 of the lumbar vertebra L4. Intermediate portions of the same braid 50' are engaged in the longitudinal passages 106 and 108 of the intermediate spacer and its ends 50'b and 50'c are engaged in the spacer 48 in exactly the same manner as that described with reference to FIGS. 2 to 4.

It can be understood that this obtains dynamic stabilization between the sacrum S and the lumbar vertebrae L5 and L4.

Naturally, it is possible to provide a larger number of simple intervertebral spacers of the type referenced 90, and that are interposed between lumbar vertebra L4 and lumbar vertebra L3, etc.; such spacers being identical to the spacer 90. This obtains dynamic stabilization between the sacrum and a larger number of lumbar vertebrae.

Figure 6:
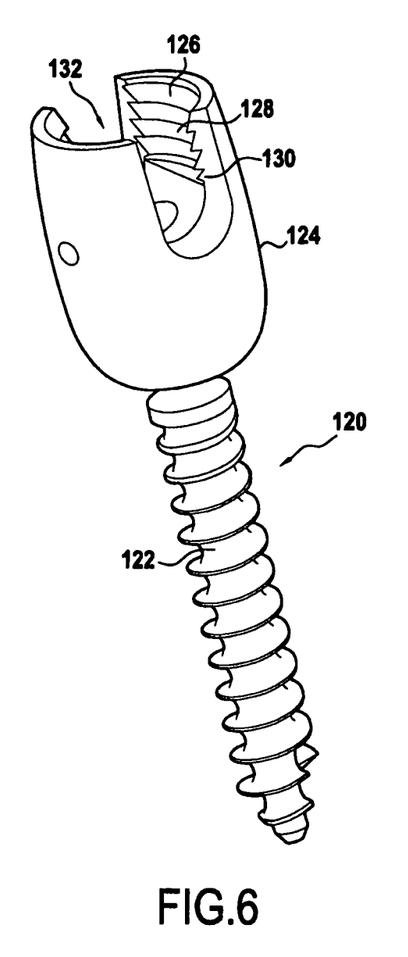
FIG. 6 is a perspective view showing a screw constituting the anchoring element for anchoring rigid rods in the sacrum.

In FIG. 6 there can be seen an example of a screw 120 suitable for constituting an anchor screw in the sacrum as described above. The screw, known as a "pedicular" screw, comprises a threaded shank 122 presenting a thread suitable for enabling it to be screwed into the sacrum, and it also possesses a head 124. The head 124 presents a circular recess 126 provided with tapping 128. The head 124 also has two notches 130 and 132 that are diametrically opposite and of dimensions suitable for receiving the ends 44c or 46c of the rigid rods. A headless set screw of the type shown under references 80 or 82 can be engaged in the tapped orifices 126 in the head of the screw for clamping purposes and thus for securing the ends of the rigid rods to the heads of the screws. It will be understood that the surgeon can initially position the appropriate portions of the ends 44c or 46c of the rods in the heads of the screws in appropriate manner for obtaining suitable positioning and clamping of the spacer 48 on the spinous process S1 of the sacrum S.

The forms of the disclosure shown and described herein are to be taken as examples of embodiments. Elements and materials may be substituted for or implemented from those illustrated and described herein, as would be apparent to those skilled in the art after having the benefit of the disclosure. Changes may be made in the elements or to the features described herein without departing from the spirit and scope of the disclosure as set forth in the following claims and their legal equivalents.

What is claimed is:

1. A dynamic stabilizer system for dynamically stabilizing the sacrum and at least lumbar vertebra L5, comprising:
    a first anchoring member for being implanted at a first location in said sacrum;
    a second anchoring member for being implanted at a second location in said sacrum, wherein said first location and said second location are distinct locations in said sacrum;
    a mechanical fastener element comprising a first end and a second end for securely fixing said mechanical fastener element on a spinous process of a lumbar vertebra L5, said mechanical fastener element including at least a first spacer configured to be interposed between said spinous process of said lumbar vertebra L5 and a process S1 of said sacrum;
    a flexible tie configured to cooperate with said spinous process of said lumbar vertebra L5, said flexible tie comprising two ends secured to said first spacer;
    a first rod comprising a first end for securing onto said first end of said mechanical fastener element and a second end for securing to said first anchoring member, wherein a point on said first rod at which said second end of said first rod is secured to said first anchoring member is adjustable; and a second rod comprising a first end for securing onto said second end of said mechanical fastener element and a second end for securing to said second anchoring member, wherein a point on said second rod at which said second end of said second rod is secured to said second anchoring member is adjustable, wherein said first rod and said second rod are two distinct rods;

wherein said first spacer comprises a first end and a second end, wherein each of said first and second ends of said first spacer comprises a locking member for locking said first end of either said first rod or said second rod;

wherein said first spacer comprises two locking elements for locking said two ends of said flexible tie; and wherein each locking member and the corresponding locking element comprise a first orifice for receiving said first end of either said first rod or said second rod, a second orifice opening out into said first orifice for receiving one of said two ends of said flexible tie, and a controllable clamping member acting in a clamped position to secure said one of said two ends of said flexible tie and said first end of either said first rod or said second rod.

2. The dynamic stabilizer system of claim 1, wherein said flexible tie is constructed for completely surrounding said spinous process, said first and second ends of said mechanical fastener element being constituted by portions of said flexible tie.

3. The dynamic stabilizer system of claim 2, wherein said mechanical fastener element further comprises two securing parts constructed for being held on either side of said spinous process by said flexible tie, said first end of each of said first and second distinct rods being secured to one of said two securing parts.

4. The dynamic stabilizer system of claim 2, wherein said flexible tie has two tie portions, each portion configured for surrounding a portion of said spinous process of said lumbar vertebra, said two tie portions and said first and second ends of said mechanical fastener element being constituted by interconnected ends of said two tie portions.

5. The dynamic stabilizer system of claim 1, wherein said mechanical fastener element further comprises a second spacer configured to be interposed between the spinous processes of lumbar vertebrae L5 and L4, said flexible tie cooperating with said second spacer for partially surrounding the process of lumbar vertebra L4.

6. The dynamic stabilizer system of claim 5, wherein said second spacer comprises two side passages in which two intermediate portions of said flexible tie are freely engaged.

7. The dynamic stabilizer system of claim 1, wherein each of said first and second anchoring members comprises a screw having a head for cooperating with said second end of either said first rod or said second rod.

8. The dynamic stabilizer system of claim 7, wherein said head of each screw comprises a recess for receiving said second end of either said first rod or said second rod and a clamping element for acting in a position to prevent said second end of either said first rod or said second rod from moving relative to said head of said screw, wherein said position is adjustable.

9. The dynamic stabilizer system of claim 1, wherein said first rod and said second rod are rigid.

10. A dynamic stabilizer system for dynamically stabilizing the sacrum and at least lumbar vertebra L5, comprising:

a first anchoring member for being implanted at a first location in said sacrum;

a second anchoring member for being implanted at a second location in said sacrum, wherein said first location and said second location are distinct locations in said sacrum;

a mechanical fastener element comprising:
 a first end and a second end for securely fixing said mechanical fastener element on a spinous process of said lumbar vertebra L5;
 at least a first spacer configured to be interposed between said spinous process of said lumbar vertebra L5 and a process S1 of said sacrum; and
 a flexible tie for cooperating with said spinous process of said lumbar vertebra L5, said flexible tie comprising two ends secured to said first spacer;

a first rod comprising a first end for securing onto said first end of said mechanical fastener element and a second end for securing to said first anchoring member, wherein a point on said first rod at which said second end of said first rod is secured to said first anchoring member is adjustable; and a second rod comprising a first end for securing onto said second end of said mechanical fastener element and a second end for securing to said second anchoring member, wherein a point on said second rod at which said second end of said second rod is secured to said second anchoring member is adjustable, wherein said first rod and said second rod are two distinct rods;

wherein said mechanical fastener element further comprises a second spacer configured to be interposed between the spinous processes of lumbar vertebrae L5 and L4, said flexible tie cooperating with said second spacer for partially surrounding the process of lumbar vertebra L4;

wherein said first spacer comprises a first end and a second end, wherein each of said first and second ends of said first spacer comprises a locking member for locking said first end of either said first rod or said second rod;

wherein said first spacer comprises two locking elements for locking said two ends of said flexible tie; and wherein each locking member and the corresponding locking element comprise a first orifice for receiving said first end of either said first rod or said second rod, a second orifice opening out into said first orifice for receiving one of said two ends of said flexible tie, and a controllable clamping member acting in a clamped position to secure said one of said two ends of said flexible tie and said first end of either said first rod or said second rod.

11. The dynamic stabilizer system of claim 10, wherein said second spacer comprises two side passages in which two intermediate portions of said flexible tie are freely engaged.

12. The dynamic stabilizer system of claim 10, wherein said flexible tie has two tie portions, each surrounding a portion of said spinous process of said lumbar vertebra, said two tie portions and said first and second ends of said mechanical fastener element being constituted by interconnected ends of said two tie portions.

13. A dynamic stabilizer system for dynamically stabilizing a sacrum and at least one lumbar vertebra, comprising:

a first anchoring member for being implanted at a first location in the sacrum;

a second anchoring member for being implanted at a second location in the sacrum, wherein the first location and the second location are distinct locations in the sacrum;

a first spacer configured to be interposed between a spinous process of the lumbar vertebra and a process of the sacrum;

a flexible tie for securing the first spacer to the lumbar vertebra, the flexible tie comprising a first end portion, a second end portion, and an intermediate portion between the first and second end portions configured to extend around the spinous process of the lumbar vertebra;

a first rod comprising a first end for securing to the first spacer and a second end for securing to the first anchoring member;

a second rod comprising a first end for securing to the first spacer and a second end for securing to the second anchoring member;

wherein the first end of the first rod is inserted into a first opening in the first spacer and the first end of the second rod is inserted into a second opening in the first spacer;

a first locking member configured to simultaneously secure the first end of the first rod and the first end portion of the flexible tie to the first spacer; and a second locking member configured to simultaneously secure the first end of the second rod and the second end portion of the flexible tie to the first spacer;

wherein the first end portion of the flexible tie is inserted into a third opening in the first spacer intersecting the first opening in the first spacer;

wherein the second end portion of the flexible tie is inserted into a fourth opening in the first spacer intersecting the second opening in the first spacer;

wherein the first locking member is configured to bare against the first end of the first rod to exert pressure on the first end of the first rod and exert pressure on the first end portion of the flexible tie.

14. The dynamic stabilizer system of claim 13, wherein the second locking member is configured to bare against the first end of the second rod to exert pressure on the first end of the second rod and exert pressure on the second end portion of the flexible tie.

15. The dynamic stabilizer system of claim 14, wherein the first end portion of the flexible tie is positioned between the first end of the first rod and a first surface of the first spacer, and the second end portion of the flexible tie is positioned between the first end of the second rod and a second surface of the first spacer.

* * * * *